(12) United States Patent
Joshi et al.

(10) Patent No.: US 11,311,426 B2
(45) Date of Patent: Apr. 26, 2022

(54) ABSORBENT ARTICLE

(71) Applicant: Kimberly-Clark Worldwide, Inc., Neenah, WI (US)

(72) Inventors: Vishal Y Joshi, Antioquia (CO); Jose A Peredo, Sao Paulo (BR); Natalia Hoyos, Antioquia (CO)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 611 days.

(21) Appl. No.: 16/095,399

(22) PCT Filed: Apr. 27, 2016

(86) PCT No.: PCT/US2016/029480
§ 371 (c)(1),
(2) Date: Oct. 22, 2018

(87) PCT Pub. No.: WO2017/188940
PCT Pub. Date: Nov. 2, 2017

(65) Prior Publication Data
US 2019/0133838 A1    May 9, 2019

(51) Int. Cl.
| | |
|---|---|
| *A61F 13/15* | (2006.01) |
| *A61F 13/475* | (2006.01) |
| *A61F 13/472* | (2006.01) |
| *A61F 13/539* | (2006.01) |
| *A61F 13/56* | (2006.01) |
| *A61F 13/535* | (2006.01) |

(Continued)

(52) U.S. Cl.
CPC ............ *A61F 13/475* (2013.01); *A61F 13/15* (2013.01); *A61F 13/472* (2013.01); *A61F 13/539* (2013.01); *A61F 13/5616* (2013.01); *A61F 13/535* (2013.01); *A61F 13/538* (2013.01); *A61F 2013/15487* (2013.01); *A61F 2013/530007* (2013.01); *A61F 2013/53908* (2013.01)

(58) Field of Classification Search
CPC ...... A61F 13/475; A61F 13/15; A61F 13/472; A61F 13/59; A61F 13/5616; A61F 13/535; A61F 13/538; A61F 2013/15487; A61F 2013/530007; A61F 2013/53908
See application file for complete search history.

(56) References Cited

U.S. PATENT DOCUMENTS

| | | |
|---|---|---|
| 4,578,071 A | 3/1986 | Buell |
| 4,804,379 A | 2/1989 | Toth et al. |

(Continued)

FOREIGN PATENT DOCUMENTS

| | | |
|---|---|---|
| CN | 1094942 A | 11/1994 |
| CN | 1142760 A | 2/1997 |

(Continued)

*Primary Examiner* — Jacqueline F Stephens
(74) *Attorney, Agent, or Firm* — Kimberly-Clark Worldwide, Inc.

(57) ABSTRACT

An absorbent article which can have a reduction in the incidence of side leakage of body exudates from the absorbent article. The absorbent article can have a topsheet layer, a backsheet layer, an absorbent core positioned between the topsheet layer and the backsheet layer, and a barrier composition positioned between the topsheet layer and the backsheet layer and bonding the topsheet layer to the backsheet layer.

15 Claims, 4 Drawing Sheets

(51) Int. Cl.
*A61F 13/538* (2006.01)
*A61F 13/53* (2006.01)

(56) References Cited

U.S. PATENT DOCUMENTS

| | | | |
|---|---|---|---|
| 4,963,139 A | 10/1990 | Dabroski | |
| 5,569,234 A * | 10/1996 | Buell | A61F 13/49009 604/396 |
| 5,728,084 A | 3/1998 | Palumbo et al. | |
| 5,762,642 A | 6/1998 | Coles et al. | |
| 5,807,367 A | 9/1998 | Dilnik et al. | |
| 5,817,079 A | 10/1998 | Bergquist et al. | |
| 5,945,175 A | 8/1999 | Yahiaoui et al. | |
| 6,004,306 A * | 12/1999 | Robles | A61F 13/49009 604/385.21 |
| 6,017,336 A | 1/2000 | Sauer | |
| 6,506,959 B2 | 1/2003 | Hamajima et al. | |
| 6,548,732 B2 | 4/2003 | Erdman et al. | |
| 6,761,955 B2 | 7/2004 | Mizutani et al. | |
| 7,166,094 B2 | 1/2007 | Glaug et al. | |
| 7,291,763 B2 | 11/2007 | Mirle et al. | |
| 7,598,427 B2 | 10/2009 | Ragnarson et al. | |
| 7,824,385 B2 | 11/2010 | Ecker et al. | |
| 8,338,659 B2 | 12/2012 | Collins et al. | |
| 8,461,411 B2 | 6/2013 | Digiacomantonio et al. | |
| 2005/0215967 A1 | 9/2005 | Toro et al. | |
| 2006/0069375 A1 | 3/2006 | Waksmundzki et al. | |
| 2006/0160452 A1 * | 7/2006 | Mirle | B32B 27/02 442/381 |
| 2009/0036856 A1 | 2/2009 | Woltman et al. | |
| 2010/0069864 A1 | 3/2010 | Berland et al. | |
| 2010/0152691 A1 | 6/2010 | Seidling et al. | |
| 2010/0305529 A1 * | 12/2010 | Ashton | A61F 13/42 604/361 |
| 2011/0319855 A1 | 12/2011 | Lash | |
| 2012/0265161 A1 | 10/2012 | Banks et al. | |
| 2015/0148765 A1 | 5/2015 | Wang et al. | |

FOREIGN PATENT DOCUMENTS

| | | |
|---|---|---|
| CN | 1202099 A | 12/1998 |
| CN | 1207662 A | 2/1999 |
| CN | 1433290 A | 7/2003 |
| CN | 1575786 A | 2/2005 |
| CN | 1791373 A | 6/2006 |
| CN | 1970670 A | 5/2007 |
| EP | 1842513 B1 | 9/2014 |
| ES | 2176087 | 11/2002 |

* cited by examiner

ABSORBENT ARTICLE

BACKGROUND OF THE DISCLOSURE

Products such as absorbent articles are often used to collect and retain human body exudates containing, for example, urine, menses and/or blood. Comfort, absorbency, and discretion are three main product attributes and areas of concern for the wearer of the product. In particular, a wearer is often interested in knowing that such products will absorb significant volumes of body exudates with minimal leakage in order to protect their undergarments, outer garments, or bedsheets from staining, and that such products will help them avoid the subsequent embarrassment brought on by such staining.

Currently, a wide variety of products for absorption of body exudates are available in the form of feminine pads, sanitary napkins, panty shields, pantiliners, and incontinence devices. These products generally have an absorbent core positioned between a body-facing liquid permeable topsheet layer and a garment-facing liquid impermeable backsheet layer. The edges of the topsheet and the backsheet layers are often bonded together at their periphery to form a seal to contain the absorbent core and body exudates received into the product through the topsheet layer. In use, such products are typically positioned in the crotch portion of an undergarment for absorption of the body exudates and a garment attachment adhesive on the backsheet layer can be used to attach the product to the inner crotch portion of the undergarment. Some of these products can also include wings for wrapping about the wearer's undergarment to further secure the product to the undergarment and to protect the undergarment from staining. Such wings are frequently made from lateral extensions of the topsheet and/or backsheet layers.

A common drawback with current commercial absorbent articles is the leakage of body exudates from the absorbent article, and in particular, leakage of body exudates from the sides of the absorbent article. Leakage of body exudates from absorbent articles is generally attributed to a high concentration of body exudates at the point of initial insult into the absorbent article. This could be the result of a sudden release of body exudate onto the absorbent article, overloading the absorption capacity of the absorbent article, or the result of a prolonged steady discharge which may have caused the absorbent core in the absorbent article to become super-saturated and unable to accept, to a large degree, additional body exudates from the wearer of the absorbent article.

Using a sanitary napkin as an illustration, it has been suggested that 20-25% of sanitary napkins will experience side leakage. One reason for this is that, when worn, the sanitary napkin can become deformed due to dynamic forces generated as the wearer moves or alters her stationary position. Generally, the sanitary napkin deforms by bunching, twisting, and roping which are all well known in the art. The greatest deformation normally occurs within the part of the absorbent article which in use is located in the narrowest space between the wearer's thighs. As a result of the deformation the surface area of the sanitary napkin is greatly reduced which may lead to the soiling of the wearer's body, typically around the thigh region, and the wearer's undergarment.

A wide variety of special components and adaptations have been introduced in absorbent articles in order to reduce or eliminate the incidence of side leakage. For instance, many absorbent articles include elastic structures positioned along the sides of the absorbent core and adjacent at least one of the topsheet layer or the backsheet layer. The elastic structures are intended to gather at least a portion of the side edge of the absorbent article to form walls, barriers, side seals, and the like, to impede the flow of body exudate past the side edges of the absorbent article. In addition to the elastic structures, absorbent articles have also included elasticized containment flaps which project from the surface of the topsheet layer in an attempt to control the movement of body exudates toward the side edges of the absorbent article.

A problem associated with barriers, walls, and the like, is that to prevent body exudates from soiling the wearer, the barriers are relatively tall. During use, their size makes them uncomfortable for the wearer and the barrier may fold over and obstruct the absorbent surface. This, in turn, may contribute to the soiling of the wearer instead of preventing the soiling of the wearer. Additionally, such barriers are generally located on the topsheet layer of the absorbent article and cannot prevent movement of body exudates within the absorbent article, such as between the topsheet layer and the backsheet layer. Such movement of body exudates between the topsheet layer and the backsheet layer can lead to leakage of the body exudates from the absorbent article.

There remains a need for an absorbent article that will be comfortable to wear while decreasing the chance of side leakage associated with the use of the absorbent article.

SUMMARY OF THE DISCLOSURE

An absorbent article characterized by comprising an anterior portion, a posterior portion, and a central portion; a topsheet layer and a backsheet layer; an absorbent core having an opposing pair of transverse direction edges and an opposing pair of longitudinal direction edges and being positioned between the topsheet layer and the backsheet layer; the topsheet layer and the backsheet layer extending beyond each of the transverse direction edges and longitudinal direction edges of the absorbent core and being peripherally bonded together to form a sealed peripheral region; and a barrier composition positioned between the topsheet layer and the backsheet layer, the barrier composition forming a portion of the sealed peripheral region, the barrier composition comprising a polymeric layer and an adhesive layer.

In various embodiments, the barrier composition is non-swelling. In various embodiments, the polymeric layer is hydrophilic and the adhesive layer is hydrophobic. In various embodiments, the polymeric layer comprises a polymer, an adjunct, and a crosslinking agent. In various embodiments, the polymer is polyvinyl alcohol. In various embodiments, the adjunct is polyvinyl pirrolidone. In various embodiments, the crosslinking agent is sodium tetraborate decahydrate.

In various embodiments, the barrier composition is located in the central portion of the absorbent article. In various embodiments, the barrier composition is further located in at least a portion of the posterior portion of the absorbent article. In various embodiments, the barrier composition is further located in at least a portion of the anterior portion of the absorbent article. In various embodiments, the barrier composition is located in a portion of the central portion of the absorbent article and a portion of the posterior portion of the absorbent article.

In various embodiments, the absorbent article further comprises a pair of wings formed as extensions of the topsheet layer and the backsheet layer. In various embodiments, the barrier composition is positioned between the topsheet layer and the backsheet layer forming each of the wings. In various embodiments, the wings are located in the central portion of the absorbent article. In various embodiments, the wings are located in at least a portion of the central portion of the absorbent article and at least a portion of the anterior region of the absorbent article. In various embodiments, wherein the absorbent article further comprises a second pair of wings.

Figure 1:
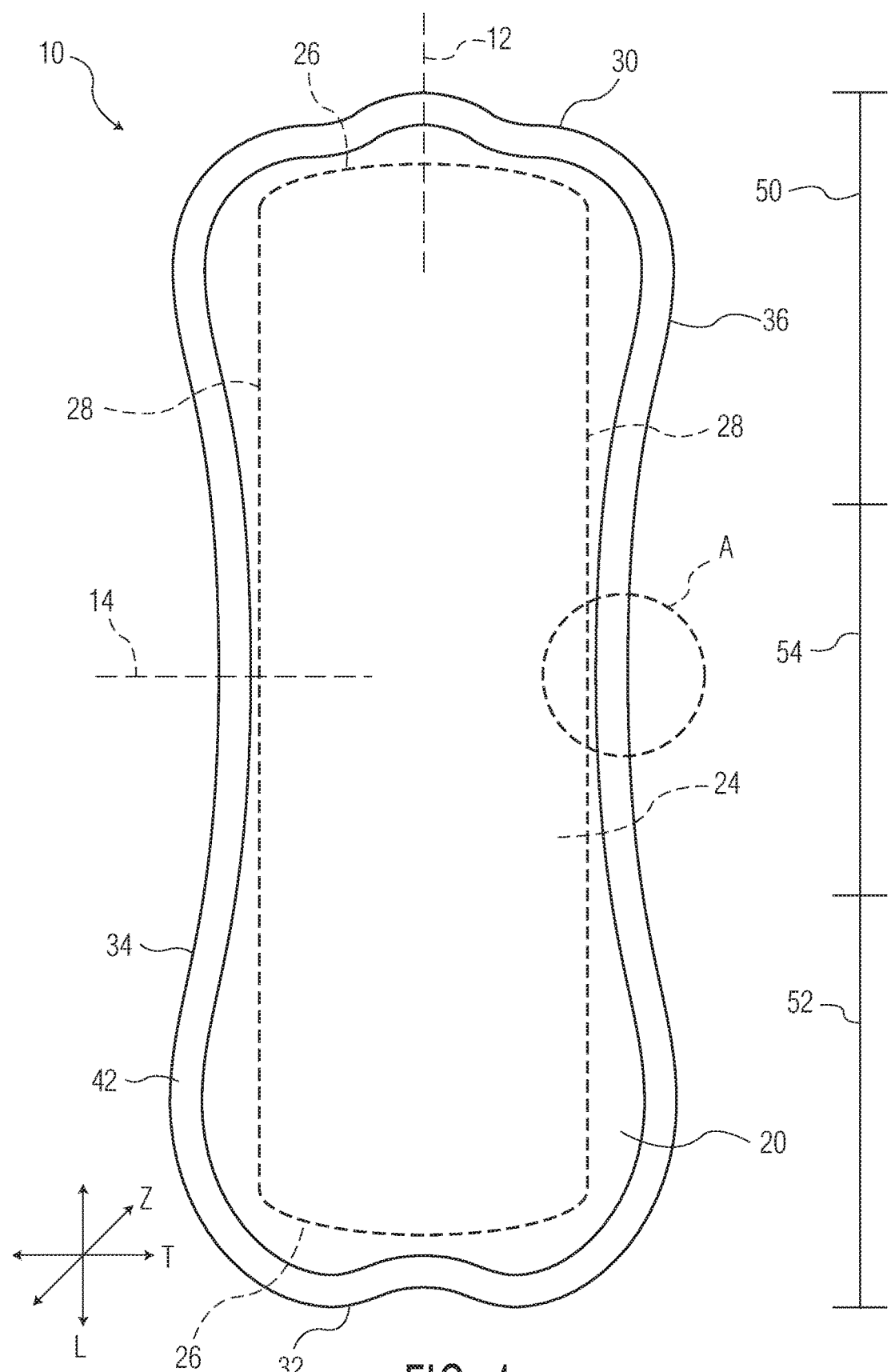
FIG. 1 is a top down view of an embodiment of an absorbent article.

Repeat use of reference characters in the present specification and drawings is intended to represent the same or analogous features or elements of the disclosure.

DETAILED DESCRIPTION OF THE DISCLOSURE

The present disclosure is generally directed towards an absorbent article which can have a reduction in the incidence of side leakage of body exudates from the absorbent article. The absorbent article described herein can have a topsheet layer, a backsheet layer, an absorbent core positioned between the topsheet layer and the backsheet layer, and a barrier composition positioned between the topsheet layer and the backsheet layer and bonding the topsheet layer to the backsheet layer.

Definitions:

As used herein, the term "absorbent article" refers herein to a garment or other end-use personal care absorbent article, including, but not limited to, catamenial products, such as sanitary napkins, feminine pads, pantiliners, and panty shields, incontinence devices, and the like.

As used herein, the term "airlaid" refers herein to a web manufactured by an airlaying process. In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

As used herein, the term "bonded" refers herein to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form one fiber. Conjugate fibers are also sometimes referred to as bicomponent fibers or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea" arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al. each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10 or 20 gsm to about 120, 125 or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the terms "superabsorbent polymer," "superabsorbent" or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in part on ionicity (a factor of the ionic concentration of the aqueous solution), and the SAP functional polar groups that have an affinity for water. SAP are typically made from the polymerization of acrylic acid blended with sodium hydroxide in the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating on another material or fiber.

Absorbent Article:

The present disclosure is generally directed towards an absorbent article which can have a reduction in the incidence of side leakage of body exudates from the absorbent article. The absorbent article described herein can have a topsheet layer, a backsheet layer, an absorbent core positioned between the topsheet layer and the backsheet layer, and a barrier composition positioned between the topsheet layer and the backsheet layer and bonding the topsheet layer to the backsheet layer.

Figure 2:
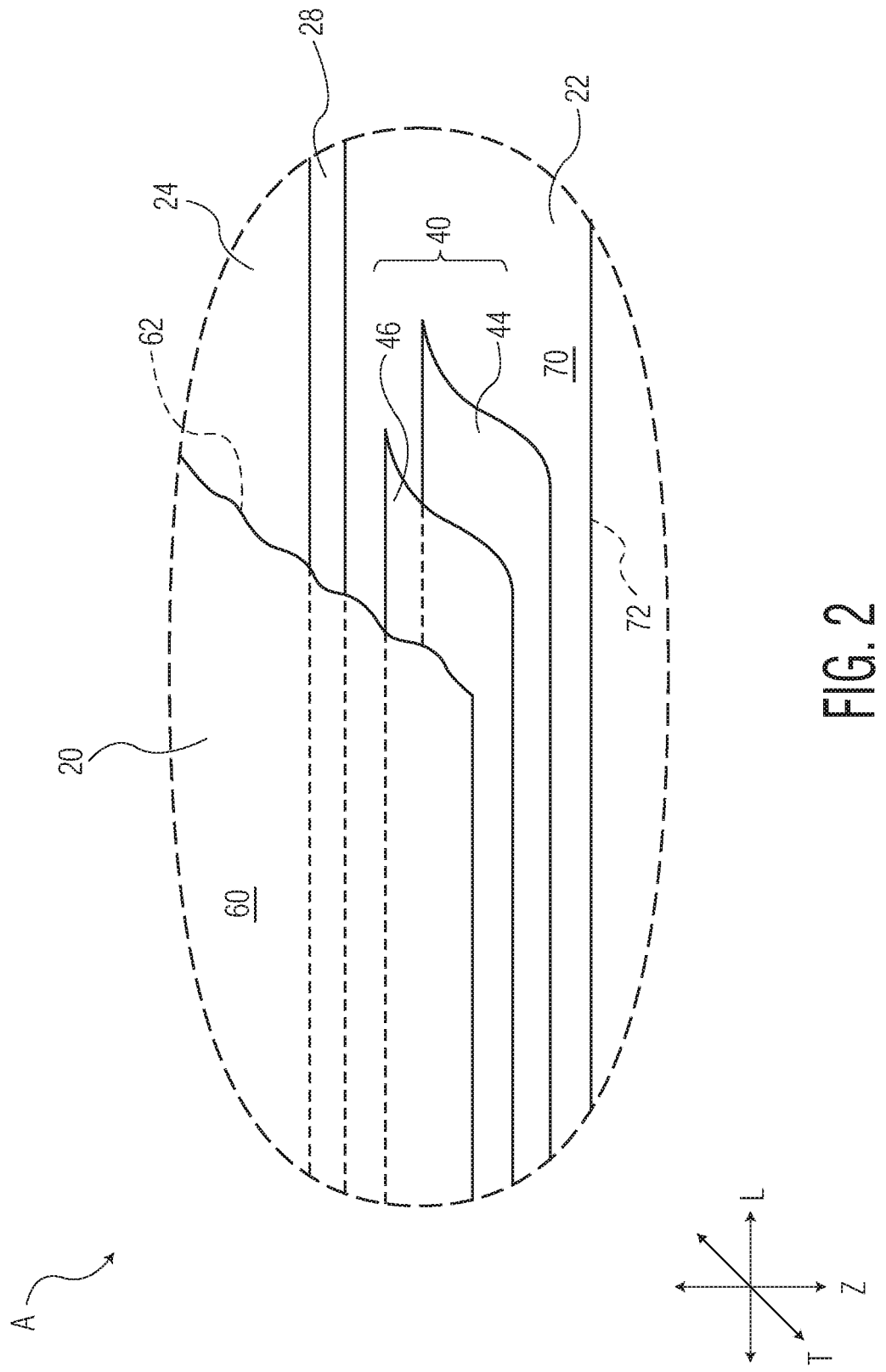
FIG. 2 is a perspective view of an exploded portion of the absorbent article of FIG. 1 with a portion removed for clarity.

Referring to FIGS. 1 and 2, FIG. 1 provides an illustration of a top view of an exemplary embodiment of an absorbent article 10 and FIG. 2 provides an illustration of a perspective view of an exploded portion of the absorbent article 10 of FIG. 1 at portion A.

The absorbent article 10 can have a longitudinal direction (L), a transverse direction (T), and a depth direction (Z). The absorbent article 10 can have a longitudinal axis 12 and a transverse axis 14. The absorbent article 10 can have a wearer facing, liquid permeable topsheet layer 20 and a garment facing, liquid impermeable backsheet layer 22. An absorbent core 24 can be positioned between the topsheet layer 20 and the backsheet layer 22. The absorbent article 10 can have a first transverse direction end edge 30, a second transverse direction end edge 32 opposite the first transverse direction end edge 30, and a pair of opposing longitudinal direction side edges, 34 and 36. In various embodiments, the absorbent article 10 can take on various geometries but will generally have a pair of opposing transverse direction end edges, 30 and 32, and a pair of opposing longitudinal direction side edges, 34 and 36.

The absorbent article 10 can have an anterior portion 50, a posterior portion 52, and a central portion 54 extending between the anterior portion 50 and the posterior portion 52. In general, the anterior portion 50 of the absorbent article 10 is adapted to be worn towards the front of the wearer, the central portion 54 is adapted to be worn proximate the wearer's crotch, and the posterior portion 52 is adapted to be worn towards the rear of the wearer. In various embodiments, the absorbent article 10 can have a length as measured in the longitudinal direction (L) between the transverse direction end edges, 30 and 32, and the anterior portion 50 can be defined as the front third of the absorbent article length, the central portion 54 can be defined as the center third of the absorbent article length, and the posterior portion 52 can be defined as the rear third of the absorbent article length. It is to be understood that the lengths of each of the anterior portion 50, the central portion 54 and the posterior portion 52 can vary as deemed suitable for usage of the absorbent article 10.

The topsheet layer 20 and the backsheet layer 22 can both extend beyond the outermost peripheral edges, such as transverse direction edges 26 and longitudinal direction edges 28, of the absorbent core 24 and can be peripherally bonded together to form a sealed peripheral region 42. A barrier composition 40 is positioned between the topsheet layer 20 and the backsheet layer 22. The barrier composition 40 bonds the topsheet layer 20 to the backsheet layer 22 forming the sealed peripheral region 42 and also provides a barrier to reduce leakage of body exudates contained within the absorbent article 10.

Current commercially available absorbent articles can experience leakage of body exudates as a result of void spaces existing between a topsheet layer and a backsheet layer of the absorbent article in a sealed peripheral region of the absorbent article. A construction adhesive is typically sprayed onto a material, such as the backsheet layer, and brought into contact with the topsheet layer to form a peripheral seal for the absorbent article. The spraying of the construction adhesive can result in droplets of construction adhesive surrounded by areas of the backsheet layer where no construction adhesive is present. When the backsheet layer and the topsheet layer are brought together to form the peripheral seal, the portions of the backsheet material without a presence of construction adhesive will form void spaces between the topsheet layer and the backsheet layer through which body exudates can escape from the absorbent article. The barrier composition 40 of the current disclosure can reduce the incidence of leakage of the body exudates from the absorbent article 10.

The barrier composition 40 is composed of a first layer of material and a second layer of material. The first layer of the barrier composition 40 is a polymeric layer 44 and the second layer of the barrier composition 40 is an adhesive layer 46. The polymeric layer 44 and the adhesive layer 46 reduce and/or eliminate incidence of leakage of body exudates contained within the absorbent article 10. The polymeric layer 44 can fill any void spaces which would otherwise be present between the topsheet layer 20 and the backsheet layer 22 such as, for example, as described above when only a sprayed-on adhesive layer 46 is present between the topsheet layer 20 and the backsheet layer 22. The barrier composition 40 can, therefore, have portions in which material forming the polymeric layer 44 and material forming the adhesive layer 46 are layered, one portion on top of the other, in the depth direction (Z) of the absorbent article 10 and can also have portions in which material forming the polymeric layer 44 and material forming the adhesive layer 46 are side-by-side in the transverse (T) and longitudinal (L) directions of the absorbent article 10.

In various embodiments, the polymeric layer 44 is hydrophilic. In various embodiments, the polymeric layer 44 is hydrophobic. In various embodiments the adhesive layer 46 is hydrophilic. In various embodiments, the adhesive layer 46 is hydrophobic. In various embodiments, both of the polymeric layer 44 and the adhesive layer 46 are hydrophobic. In various embodiments, both of the polymeric layer 44 and the adhesive layer 46 are hydrophilic. In various embodiments, at least one of the polymeric layer 44 and the adhesive layer 46 is hydrophilic and at least one of the polymeric layer 44 and the adhesive layer 46 is hydrophobic.

In various embodiments in which the polymeric layer 44 is a hydrophilic layer of the barrier composition 40, the polymeric layer 44 is formed from crosslinking a hydrophilic polymer with a hydrophilic adjunct. In various embodiments in which the polymeric layer 44 is a hydrophobic layer of the barrier composition 40, the polymeric layer 44 is formed from crosslinking a hydrophobic polymer with a hydrophobic adjunct.

In various embodiments, the polymeric layer 44 of the barrier composition 40 is formulated with materials that will result in a non-swelling, non-fugitive, non-migrating, and non-dissolvable layer in the barrier composition 40. It is preferred that the polymeric layer 44 be non-swelling so as to minimize discomfort to the wearer of the absorbent article 10. In the event that the polymeric layer 44 were to swell upon contact with body exudates, the thickness of the absorbent article 10 in the area where the polymeric layer 44 is present will increase in the depth direction (Z) which can reduce the comfort of wearing the absorbent article 10 for the wearer. An increase in the depth direction (Z) can also increase the spacing of the absorbent article 10 from the wearer's body which can lead to either actual leakage of body exudates from the absorbent article 10 or a perception to the wearer that the incidence of leakage can increase. In the event that the polymeric layer 44 is formulated with materials resulting in a fugitive, migrating, or dissolvable polymeric layer 44, the integrity of the polymeric layer 44 and the barrier composition 40 can be compromised which can result in leakage of the body exudates from the absorbent article 10.

In various embodiments in which the polymeric layer 44 is hydrophilic, the hydrophilic polymer is polyvinyl alcohol, the hydrophilic adjunct is polyvinyl pyrrolidone, and the crosslinking agent is sodium tetraborate decahydrate. In various embodiments, in which the polymeric layer 44 is hydrophilic, the hydrophilic polymer is polyvinyl alcohol, the hydrophilic adjunct is a styrene based nonionic polymeric surfactant, and the crosslinking agent is sodium tetraborate decahydrate. In various embodiments in which the polymeric layer 44 is hydrophilic, the hydrophilic polymer is polyvinyl alcohol, the hydrophilic adjunct is an acrylic acid based super absorbing material, and the crosslinking agent is sodium tetraborate decahydrate. The sodium tetraborate decahydrate is also known by other names such as sodium borate, sodium tetraborate, disodium tetraborate, and borax.

The polymeric layer 44 can be formed by combining, as an aqueous mixture, the polymer, the crosslinking agent, the adjunct, and a diluent such as water. For example, in various embodiments, the polymeric layer 44 can be composed of from about 0.5% to about 4% polyvinyl alcohol in water, from about 0.1% to about 1% sodium tetraborate decahydrate in water, and from about 0.1% to about 2% polyvinyl pyrrolidone in water. An another example, in various embodiments, the polymeric layer 44 can be composed of from about 0.5% to about 4% polyvinyl alcohol in water, from about 0.1% to about 1% sodium tetraborate decahydrate in water, and from about 0.1% to about 1% styrene bases nonionic polymeric surfactant in water. As another example, in various embodiments, the polymeric layer 44 can be composed of from about 0.5% to about 4% polyvinyl alcohol in water, from about 0.1% to about 1% sodium tetraborate decahydrate in water, and from about 0.1% to about 0.5% acrylic acid based superabsorbent material in water.

The backsheet layer 22 can have a body facing surface 70 and a garment facing surface 72. The aqueous mixture forming a liquid polymeric layer 44 can be applied to the body facing surface 70 of the backsheet layer 22. The application of the liquid polymeric layer 44 to the body facing surface 70 of the backsheet layer 22 can be via any method known to one of ordinary skill in the art such as, but not limited to, slot coating, spraying, meltblowing, etc. In various embodiments, the polymeric layer 44 can be coated on the entire surface area of the body facing surface 70 of the backsheet layer 22 of the absorbent article 10. In various embodiments, the polymeric layer 44 can be coated on less than the entire surface area of the backsheet layer 22 of the absorbent article 10.

In various embodiments, the polymeric layer 44 can be coated on at least a portion of the surface area of the body facing surface 70 of the backsheet layer 22 located in the central portion 54 of the absorbent article 10. In various embodiments, the polymeric layer 44 can be coated on at least a portion of the surface area of the body facing surface 70 of the backsheet layer 22 located in the central portion 54 and the anterior portion 50 of the absorbent article 10. In various embodiments, the polymeric layer 44 can be coated on at least a portion of the surface area of the body facing surface 70 of the backsheet layer 22 located in the central portion 54 and the posterior portion 52 of the absorbent article 10. In various embodiments, the polymeric layer 44 can be coated on at least a portion of the surface area of the body facing surface 70 of the backsheet layer 22 located in the central portion 54, the anterior portion 50, and the posterior portion 52 of the absorbent article 10.

In various embodiments, the polymeric layer 44 can be coated on the surface area of the body facing surface 70 of the backsheet layer 22 which will ultimately form the sealed peripheral region 42 in the central portion 54 of the absorbent article 10. In various embodiments, the polymeric layer 44 can be coated on the surface area of the body facing surface 70 of the backsheet layer 22 which will ultimately form the sealed peripheral region 42 in the central portion 50 and the anterior portion 50 of the absorbent article 10. In various embodiments, the polymeric layer 44 can be coated on the surface area of the body facing surface 70 of the backsheet layer 22 which will ultimately form the sealed peripheral region 42 in the central portion 50 and the posterior portion 52 of the absorbent article 10. In various embodiments, the polymeric layer 44 can be coated on the surface area of the body facing surface 70 of the backsheet layer 22 which will ultimately form the sealed peripheral region 42 in the central portion 50, the anterior portion 50, and the posterior portion 52 of the absorbent article 10.

In various embodiments, the polymeric layer 44 can be provided as a continuous coating on the surface area of the body facing surface 70 of the backsheet layer 22 wherein it is desired to position the polymeric layer 44 (e.g., entire surface area or less than the entire surface area of the body facing surface 70 of the backsheet layer 22). Providing the polymeric layer 44 as a continuous coating on the desired surface area of the backsheet layer 22 can minimize any void spaces that may otherwise occur such as, for example, in an embodiment in which the polymeric layer 44 is provided in a pattern which covers less surface area of the backsheet layer 22 than the total desired surface area.

The liquid polymeric layer 44 applied to the body facing surface 70 of the backsheet layer 22 can be dried such as, for example, by heat drying the backsheet layer 22 and polymeric layer 44 combination. As an example, the combination of the backsheet layer 22 and polymeric layer 44 can be passed through hot air which is at a temperature of about 130° C. for about 1 minute. Drying of the liquid polymeric layer 44 can result in a removal of the water from the polymeric composition and the crosslinking of the polymer and the adjunct present in the polymeric composition.

The adhesive layer 46 can be provided as any suitable construction adhesive such as is known to one of skill in the art of absorbent article manufacturing. In general, the adhesive layer 46 can have an adhesive composition which can be a poly alpha olefin (PAO), such as amorphous poly alpha olefin (APAO) or tackified amorphous poly alpha olefin (tAPAO). These construction adhesives can be produced using Ziegler-Natta catalysis and can include a variety of monomers such as propylene, ethylene, and butene. In general, these adhesives have a low degree of crystallinity as measured by Differential Scanning calorimetry (DSC).

In various embodiments, the adhesive composition of the adhesive layer 46 can have an APAO in an amount from about 50, 70, or 80% to about 85, 95, or 99% by weight of the adhesive composition. Examples of suitable APAO polymers include propylene copolymerized with butene, ethylene, and/or hexene. Two suitable neat APAO are polypropylene-1-butene APAO random copolymers, such as RT2730 or RT2723, both available from REXtac having offices in Odessa, Tex. In various embodiments, the adhesive composition of the adhesive layer 46 can include a tackifier in an amount from about 1, 5, or 15% to about 20, 30, or 50% by weight of the adhesive composition. Examples of suitable tackifiers include fully or substantially saturated (e.g., hydrogenated) C5 resins, derived from isoprene or di-cyclopentadiene (DCPD). Other suitable tackifiers include hydrocarbons derived from petroleum distillates, rosin, rosin esters, hydrogenated rosin esters, polyterpenes derived from wood, polyterpenes derived from synthetic chemicals, as well as combinations of any of these.

The topsheet layer 20 can have a body facing surface 60 and a garment facing surface 62. In various embodiments, the construction adhesive forming the adhesive layer 46 of the barrier composition 40 can be coated onto the surface area of the garment facing surface 62 of the topsheet layer 20 which will form the sealed peripheral region 42 of the absorbent article 10. In various embodiments, the adhesive layer 46 can be coated onto the surface area of the garment facing surface 62 of the topsheet layer 20 in any manner suitable such as slot coating, spraying, meltblowing, etc. In various embodiments, the adhesive layer 46 can be provided in any pattern as deemed suitable, including, but not limited to, dots, stripes, swirls, etc.

In various embodiments, the topsheet layer 20 and adhesive layer 46 combination can be brought into contact with the backsheet layer 22 and the combination of materials can be passed through a nip roll thereby bonding the layers together to form the sealed peripheral region 42. The adhesive layer 46 will be located in the entirety of the sealed peripheral region 42 and the barrier composition 40 will be located in the portions of the absorbent article 10 wherein the polymeric layer 44 is located in combination with the adhesive layer 46. As described herein, the polymeric layer 44 can be positioned in the absorbent article 10 as deemed suitable.

Figure 3:
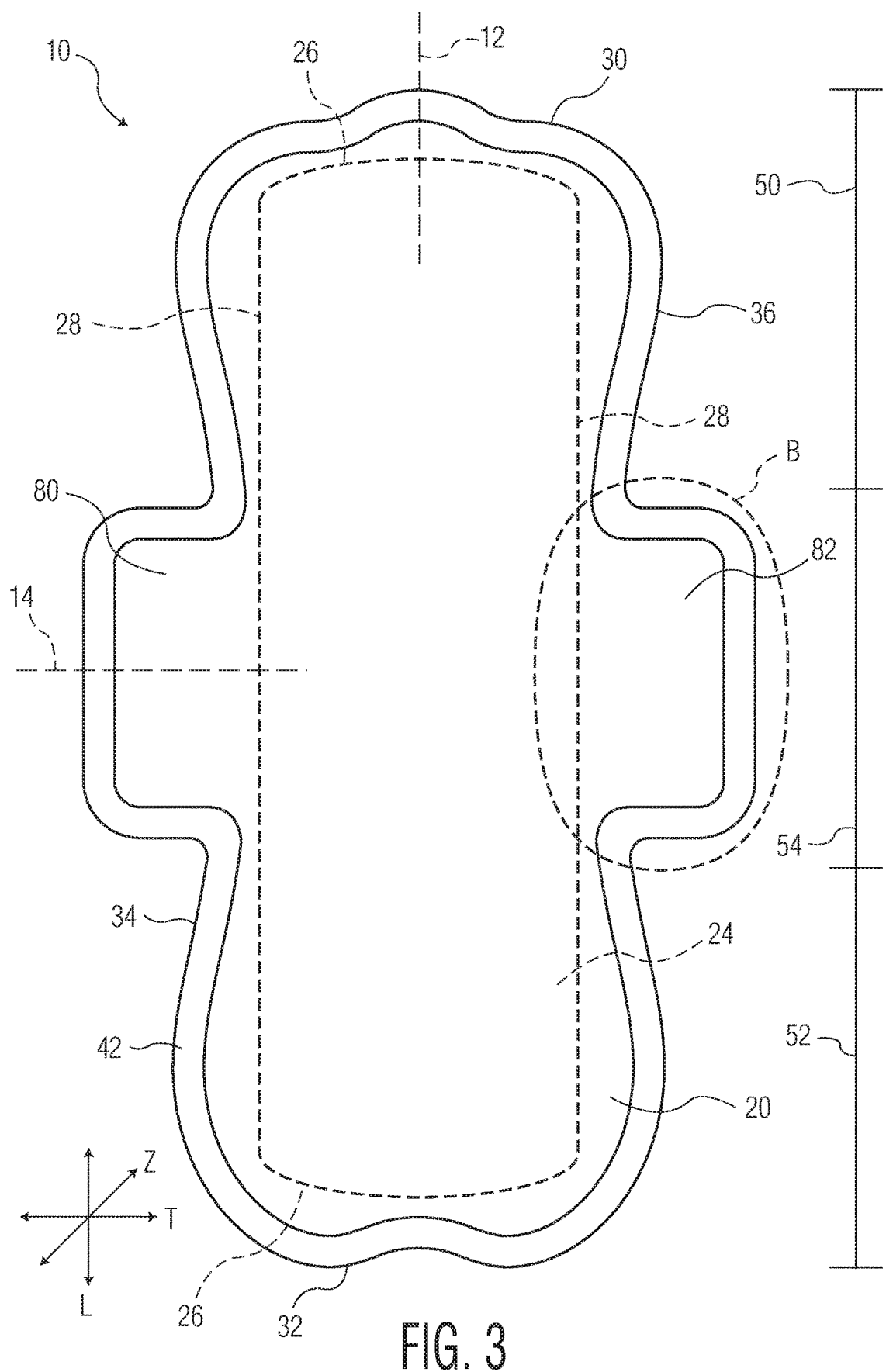
FIG. 3 is a top down view of embodiment of an absorbent article.
Figure 4:
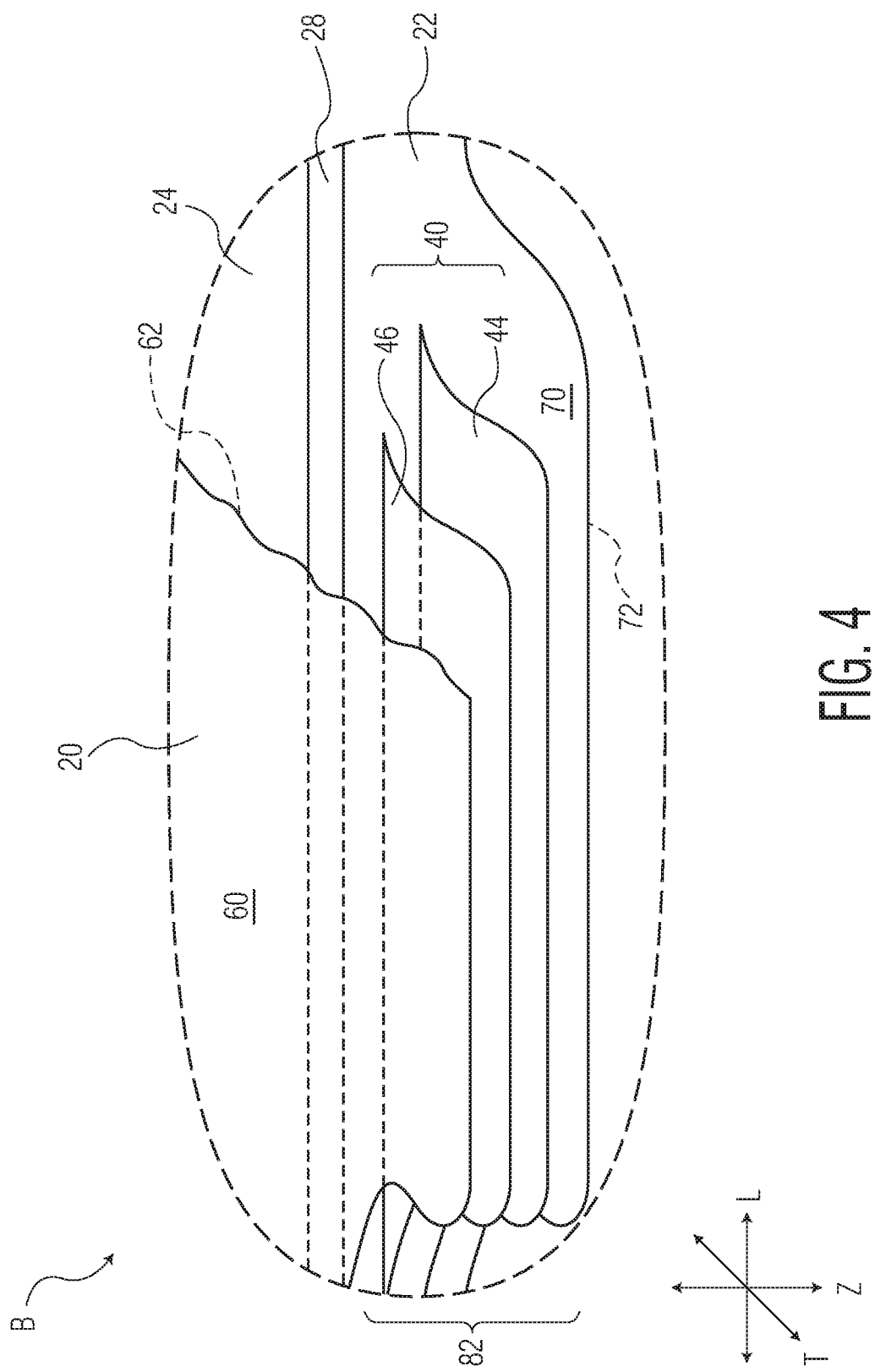
FIG. 4 is a perspective view of an exploded portion of the absorbent article of FIG. 3 with a portion removed for clarity.

Referring to FIGS. 3 and 4, FIG. 3 provides an illustration of a top view of another exemplary embodiment of an absorbent article 10 in which the absorbent article 10 has a pair of wings, 80 and 82, and FIG. 4 provides an illustration of a perspective view of an exploded portion of the absorbent article 10 of FIG. 3 at portion B.

In various embodiments, the absorbent article 10 can have a pair of wings, 80 and 82, extending outwardly, in the transverse direction (T), from the absorbent article 10. The wings, 80 and 82, can be folded downwardly and can drape over the edges of the wearer's undergarment so that the wings, 80 and 82, are disposed between the edges of the wearer's undergarment and her thighs. The wings, 80 and 82, can prevent soiling of the wearer's undergarment by forming a barrier along the edges of the undergarment. In various embodiments, the wings, 80 and 82, can be an extension of materials forming the topsheet layer 20 and/or the backsheet layer 22, such that the wings, 80 and 82, can be of a unitary construction with the absorbent article 10. In various embodiments, the wings, 80 and 82, can be constructed of materials similar to the topsheet layer 20, the backsheet layer 22 or combinations of these materials. In various embodiments, the wings, 80 and 82, can be separate elements bonded to the main body of the absorbent article 10. Examples of processes for manufacturing absorbent articles 10 and wings, 80 and 82, include, but are not limited to, those described in U.S. Pat. No. 4,059,114 to Richards, U.S. Pat. No. 4,862,574 to Hassim, et al., U.S. Pat. No. 5,342,647 to Heindel, et al., U.S. Pat. No. 7,070,672 to Alcantara, et al., U.S. Publication No., 2004/0040650 to Venturino, et al., and international publication WO1997/040804 to Emenaker, et al., each of which are hereby incorporated by reference thereto in its entirety.

Each of the wings, 80 and 82, can be provided with a barrier composition 40 having a polymeric layer 44 and an adhesive layer 46 such as described above. In various embodiments, the polymeric layer 44 can be coated on the entire surface area of the body facing surface 70 of the backsheet layer 22 forming the wings, 80 and 82, of the absorbent article 10. In various embodiments, the polymeric layer 44 can be coated on less than the entire surface area of the body facing surface 70 of the backsheet layer 22 forming the wings, 80 and 82, of the absorbent article 10. In various embodiments, the polymeric layer 44 can be coated on less than the entire surface area of the body facing surface 70 of the backsheet layer 22 forming the wings, 80 and 82, and can be positioned closer, in the transverse direction (T), to the absorbent core 24 of the absorbent article 10 than to the transversely outward perimeter edge of the wings, 80 and 82, of the absorbent article 10.

In various embodiments, such as illustrated in FIGS. 3 and 4, the wings, 80 and 82, having a barrier composition 40 can be positioned in the central portion 54 of the absorbent article 10. In various embodiments, the wings, 80 and 82, having a barrier composition 40 can be positioned in at least a portion of the central portion 54 and a portion of the anterior portion 50 of the absorbent article 10. In various embodiments, the wings, 80 and 82, having a barrier composition 40 can be positioned in at least a portion of the central portion 54 and a portion of the posterior portion 52 of the absorbent article 10. In various embodiments, the wings, 80 and 82, having a barrier composition 40 can be positioned in at least the central portion 54 and a portion of each of the anterior portion 50 and posterior portion 52 of the absorbent article 10. In various embodiments, the absorbent article 10 can have more than one pair of opposing wings and at least a portion of each pair of opposing wings can be provided with a barrier composition 40.

Topsheet Layer:

The topsheet layer 20 defines a wearer facing surface of the absorbent article 10 that may directly contact the body of the wearer and is liquid permeable to receive body exudates. The topsheet layer 20 is desirably provided for comfort and conformability and functions to direct body exudates away from the body of the wearer, through its own structure, and towards the absorbent core 24. The topsheet layer 20 desirably retains little to no liquid in its structure, so that it provides a relatively comfortable and non-irritating surface next to the skin of the wearer of the absorbent article 10.

The topsheet layer 20 can be a single layer of material, or alternatively, can be multiple layers that have been laminated together. The topsheet layer 20 can be constructed of any material such as one or more woven sheets, one or more fibrous nonwoven sheets, one or more film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a topsheet layer 20.

In various embodiments, the topsheet layer 20 can be constructed from various nonwoven webs such as meltblown webs, spunbond webs, hydroentangled spunlace webs, or through air bonded carded webs. Examples of suitable topsheet layer 20 materials can include, but are not limited to, natural fiber webs (such as cotton), rayon, hydroentangled webs, bonded carded webs of polyester, polypropylene, polyethylene, nylon, or other heat-bondable fibers (such as conjugate fibers), polyolefins, copolymers of polypropylene and polyethylene, linear low-density polyethylene, and aliphatic esters such as polylactic acid. Finely perforated films and net materials can also be used, as can laminates of/or combinations of these materials. An example of a suitable topsheet layer 20 can be a bonded carded web made of polypropylene and polyethylene such as that obtainable from Sandler Corporation, Germany. U.S. Pat. No. 4,801,494 to Datta, et al., and U.S. Pat. No. 4,908,026 to Sukiennik, et al., and WO 2009/062998 to Texol teach various other topsheet materials that may be used as the topsheet layer 20, each of which is hereby incorporated by reference thereto in its entirety. Additional topsheet layer 20 materials can include, but are not limited to, those described in U.S. Pat. No. 4,397,644 to Matthews, et al., U.S. Pat. No. 4,629,643 to Curro, et al., U.S. Pat. No. 5,188,625 to Van Iten, et al., U.S. Pat. No. 5,382,400 to Pike, et al., U.S. Pat. No. 5,533,991 to Kirby, et al., U.S. Pat. No. 6,410,823 to Daley, et al., and U.S. Publication No. 2012/0289917 to Abuto, et al., each of which is hereby incorporated by reference thereto in its entirety.

In various embodiments, the topsheet layer 20 may contain a plurality of apertures (not shown) formed therethrough to permit body exudates to pass more readily into the absorbent core 24. The apertures may be randomly or uniformly arranged throughout the topsheet layer 20. The size, shape, diameter, and number of apertures may be varied to suit an absorbent article's 10 particular needs.

In various embodiments, the topsheet layer 20 can have a basis weight ranging from about 5, 10, 15, 20 or 25 gsm to about 50, 100, 120, 125 or 150 gsm. For example, in an embodiment, a topsheet layer 20 can be constructed from a through air bonded carded web having a basis weight ranging from about 15 gsm to about 100 gsm. In another example, a topsheet layer 20 can be constructed from a through air bonded carded web having a basis weight from about 20 gsm to about 50 gsm, such as a through air bonded carded web that is readily available from nonwoven material manufacturers, such as Xiamen Yanjan Industry, Beijing, DaYuan Nonwoven Fabrics and others.

In various embodiments, the topsheet layer 20 can be at least partially hydrophilic. In various embodiments, a portion of the topsheet layer 20 can be hydrophilic and a portion of the topsheet layer 20 can be hydrophobic. In various embodiments, the portions of the topsheet layer 20 which can be hydrophobic can be either an inherently hydrophobic material or can be a material treated with a hydrophobic coating.

In various embodiments, the topsheet layer 20 can be a multicomponent topsheet layer 20 such as by having two or more different nonwoven or film materials, with the different materials placed in separate locations in the transverse direction (T) of the absorbent article 10. For example, the topsheet layer 20 can be a two layer or multicomponent material having a central portion positioned along and straddling a longitudinal axis 12 of the absorbent article 10 with lateral side portions flanking and bonded to each side edge of the central portion. The central portion can be constructed from a first material and the side portions can be constructed from a material which can be the same as or different from the material of the central portion. In such embodiments, the central portion may be at least partially hydrophilic and the side portions may be inherently hydrophobic or may be treated with a hydrophobic coating. Examples of constructions of multi-component topsheet layers 20 are generally described in U.S. Pat. No. 5,961,505 to Coe, U.S. Pat. No. 5,415,640 to Kirby, and U.S. Pat. No. 6,117,523 to Sugahara, each of which is incorporated herein by reference thereto in its entirety.

Absorbent Core:

An absorbent core 24 can be positioned between the topsheet layer 20 and the backsheet layer 22. The absorbent core 24 can generally be any single layer structure or combination of layer components, which can demonstrate some level of compressibility, conformability, be non-irritating to a wearer's skin, and capable of absorbing and retaining liquids and other body exudates. Additionally, the absorbent core 24 can provide additional capacity to absorb and retain body exudates such as menses. In various embodiments, the absorbent core 24 can be formed from a variety of different materials and can contain any number of desired layers. For example, the absorbent core 24 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of a wood pulp fluff can be identified with the trade designation NB 416, available from Weyerhaeuser Corp., and is a bleached, highly absorbent wood pulp containing primarily soft wood fibers.

In various embodiments, if desired, the absorbent core 24 can include an optional amount of superabsorbent material. Examples of suitable superabsorbent material can include poly(acrylic acid), poly(methacrylic acid), poly(acrylamide), poly(vinyl ether), maleic anhydride copolymers with vinyl ethers and α-olefins, poly(vinyl pyrrolidone), poly (vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent core 24 in any amount as desired.

Regardless of the combination of absorbent materials used in the absorbent core 24, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

The shape of the absorbent core 24 can vary as desired and can comprise any one of various shapes including, but not limited to, triangular, rectangular, dog-bone and elliptical shapes. In various embodiments, the absorbent core 24 can have a shape that generally corresponds with the overall shape of the absorbent article 10. The dimensions of the absorbent core 24 can be substantially similar to those of the absorbent article 10, however, it will be appreciated that the dimensions of the absorbent core 24 while similar, will often be less than those of the overall absorbent article 10, in order to be adequately contained therein.

By way of example, suitable materials and/or structures for the absorbent core 24 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al., each of which is hereby incorporated by reference thereto in its entirety.

As described above, in various embodiments, an absorbent core 24 can be a single layer structure and can include, for example, a matrix of cellulosic fluff and superabsorbent material. In various embodiments, an absorbent core 24 can have at least two layers of material, such as, for example, a body facing layer and a garment facing layer. In various embodiments, the two layers can be identical to each other. In various embodiments, the two layers can be different from each other. In such embodiments, the two layers can provide the absorbent article 10 with different absorption properties as deemed suitable. In various embodiments, the body facing layer of the absorbent core 24 may be constructed of an airlaid material and the garment facing layer of the absorbent core 24 may be constructed of a superabsorbent polymer-containing compressed sheet. In such embodiments, the airlaid material can have a basis weight from about 40 to about 200 gsm and the superabsorbent polymer-containing compressed sheet can be a cellulosic fluff based material that can be a combination of cellulosic pulp and SAP enclosed with a tissue carrier and having a basis weight from about 40 to about 400 gsm.

Backsheet Layer:

The backsheet layer 22 is generally liquid impermeable and is the portion of the absorbent article 10 which faces the garment of the wearer. The backsheet layer 22 can permit the passage of air or vapor out of the absorbent article 10 while still blocking the passage of liquids. Any liquid impermeable material may generally be utilized to form the backsheet layer 22. The backsheet layer 22 can be composed of a single layer or multiple layers, and these one or more layers can themselves comprise similar or different materials. Suitable material that may be utilized can be a microporous polymeric film, such as a polyolefin film of polyethylene or polypropylene, nonwovens and nonwoven laminates, and film/nonwoven laminates. The particular structure and composition of the backsheet layer 22 can be selected from various known films and/or fabrics with the particular material being selected as appropriate to provide the desired level of liquid barrier, strength, abrasion resistance, tactile properties, aesthetics and so forth. In various embodiments, a polyethylene film can be utilized that can have a thickness in the range of from about 0.2 or 0.5 mils to about 3.0 or 5.0 mils. An example of a backsheet layer 22 can be a polyethylene film such as that obtainable from Pliant Corporation, Schaumburg, Ill., USA. Another example can include calcium carbonate-filled polypropylene film. In still another embodiment, the backsheet layer 22 can be a hydrophobic nonwoven material with water barrier properties such as a nonwoven laminate, an example of which can be a spunbond, meltblown, meltblown, spunbond, four-layered laminate. The backsheet layer 22 can, therefore, be of a single or multiple layer construction, such as of multiple film layers or laminates of film and nonwoven fibrous layers. Suitable backsheet layers 22 can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and U.S. Pat. No. 6,376,095 to Cheung, et al., each of which are hereby incorporated by reference thereto in its entirety.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. An absorbent article characterized by comprising:
   a. an anterior portion, a posterior portion, and a central portion;
   b. a topsheet layer having a body facing surface and a garment facing surface, and a backsheet layer having a body facing surface and a garment facing surface;
   c. an absorbent core having an opposing pair of transverse direction edges and an opposing pair of longitudinal direction edges and being positioned between the topsheet layer and the backsheet layer;
   d. the topsheet layer and the backsheet layer extending beyond each of the transverse direction edges and longitudinal direction edges of the absorbent core and being peripherally bonded together to form a sealed peripheral region; and
   e. a barrier composition positioned between the topsheet layer and the backsheet layer, the barrier composition forming a portion of the sealed peripheral region, the barrier composition comprising a polymeric layer coated on the body facing surface of the backsheet layer and an adhesive layer coated on the garment facing surface of the topsheet layer;
   wherein the barrier composition is located in the central portion of the absorbent article.

2. The absorbent article of claim 1 wherein the barrier composition is non-swelling.

3. The absorbent article of claim 1 wherein the polymeric layer is hydrophilic and the adhesive layer is hydrophobic.

4. The absorbent article of claim 1 wherein the polymeric layer comprises a polymer, an adjunct, and a crosslinking agent.

5. The absorbent article of claim 4 wherein the polymer is polyvinyl alcohol.

6. The absorbent article of claim 4 wherein the adjunct is polyvinyl pyrrolidone.

7. The absorbent article of claim 4 wherein the crosslinking agent is sodium tetraborate decahydrate.

8. The absorbent article of claim 1 wherein the barrier composition is further located in at least a portion of the posterior portion of the absorbent article.

9. The absorbent article of claim 8 wherein the barrier composition is further located in at least a portion of the anterior portion of the absorbent article.

10. The absorbent article of claim 1 wherein the barrier composition is located in a portion of the central portion of the absorbent article and a portion of the posterior portion of the absorbent article.

11. The absorbent article of claim 1 further comprising a pair of wings formed as extensions of the topsheet layer and the backsheet layer.

12. The absorbent article of claim 11 wherein the barrier composition is positioned between the topsheet layer and the backsheet layer forming each of the wings.

13. The absorbent article of claim 11 wherein the wings are located in the central portion of the absorbent article.

14. The absorbent article of claim 11 wherein the wings are located in at least a portion of the central portion of the absorbent article and at least a portion of the anterior region of the absorbent article.

15. The absorbent article of claim 11 further comprising a second pair of wings.

* * * * *